United States Patent
Ferreira et al.

(10) Patent No.: US 7,018,412 B2
(45) Date of Patent: Mar. 28, 2006

(54) ALLOGRAFT SPINAL IMPLANT

(75) Inventors: Rui J. Ferreira, Newark, NJ (US); Jeffrey D. Schwardt, Morristown, NJ (US); Donald Kucharzyk, Crown Point, IN (US)

(73) Assignee: EBI, L.P., Parsippany, NJ (US)

( * ) Notice: Subject to any disclaimer, the term of this patent is extended or adjusted under 35 U.S.C. 154(b) by 0 days.

(21) Appl. No.: 10/225,090

(22) Filed: Aug. 20, 2002

(65) Prior Publication Data

US 2003/0069640 A1    Apr. 10, 2003

Related U.S. Application Data

(60) Provisional application No. 60/313,600, filed on Aug. 20, 2001, provisional application No. 60/313,602, filed on Aug. 20, 2001.

(51) Int. Cl.
*A61F 2/44* (2006.01)

(52) U.S. Cl. ............... 623/17.11; 623/17.15; 623/17.16; 606/61; 606/99

(58) Field of Classification Search ......... 623/17.11, 623/17.16, 17.15; 606/61, 99
See application file for complete search history.

(56) References Cited

U.S. PATENT DOCUMENTS

| | | | |
|---|---|---|---|
| 2,677,369 A | 4/1954 | Knowles | 128/92 |
| 4,714,469 A | 12/1987 | Kenna | 623/17 |
| 4,904,261 A | 2/1990 | Dove et al. | 623/17 |
| 4,950,296 A | 8/1990 | McIntyre | 623/16 |
| 5,112,354 A | 5/1992 | Sires | 623/16 |
| 5,489,308 A * | 2/1996 | Kuslich et al. | 623/17.11 |
| 5,728,159 A | 3/1998 | Stroever et al. | 623/16 |
| 5,814,084 A | 9/1998 | Grivas et al. | 623/16 |
| 5,865,845 A * | 2/1999 | Thalgott | 623/17.16 |
| 5,888,222 A | 3/1999 | Coates et al. | 623/17 |
| 5,989,289 A | 11/1999 | Coates et al. | 623/17 |
| 6,111,164 A | 8/2000 | Rainey et al. | 623/16 |
| 6,143,032 A | 11/2000 | Schafer et al. | 623/17.11 |
| 6,143,033 A | 11/2000 | Paul et al. | 623/17.11 |
| 6,206,923 B1 | 3/2001 | Boyd et al. | 623/17.11 |
| 6,277,149 B1 * | 8/2001 | Boyle et al. | 623/17.16 |
| 6,350,283 B1 | 2/2002 | Michelson | 623/17.11 |
| 6,511,509 B1 * | 1/2003 | Ford et al. | 623/23.5 |
| 2001/0039458 A1 | 11/2001 | Boyer, II et al. | 623/23.63 |
| 2001/0041941 A1 | 11/2001 | Boyer, II et al. | 623/23.52 |
| 2002/0091447 A1 | 7/2002 | Shimp et al. | 623/17.16 |
| 2002/0138143 A1 | 9/2002 | Grooms et al. | 623/17.11 |

FOREIGN PATENT DOCUMENTS

EP    0 599 419 A2    6/1994

* cited by examiner

*Primary Examiner*—Thomas Barrett
*Assistant Examiner*—Christopher D Prone
(74) *Attorney, Agent, or Firm*—Harness, Dickey & Pierce, P.L.C.

(57) ABSTRACT

An allograft spinal implant includes a generally planar superior end face, a generally planar inferior end face and a generally cylindrical sidewall. The generally cylindrical sidewall extends between the superior end face and the inferior end face. At least one of the superior end face and the inferior end face includes a plurality of concentric circular ridges.

23 Claims, 13 Drawing Sheets

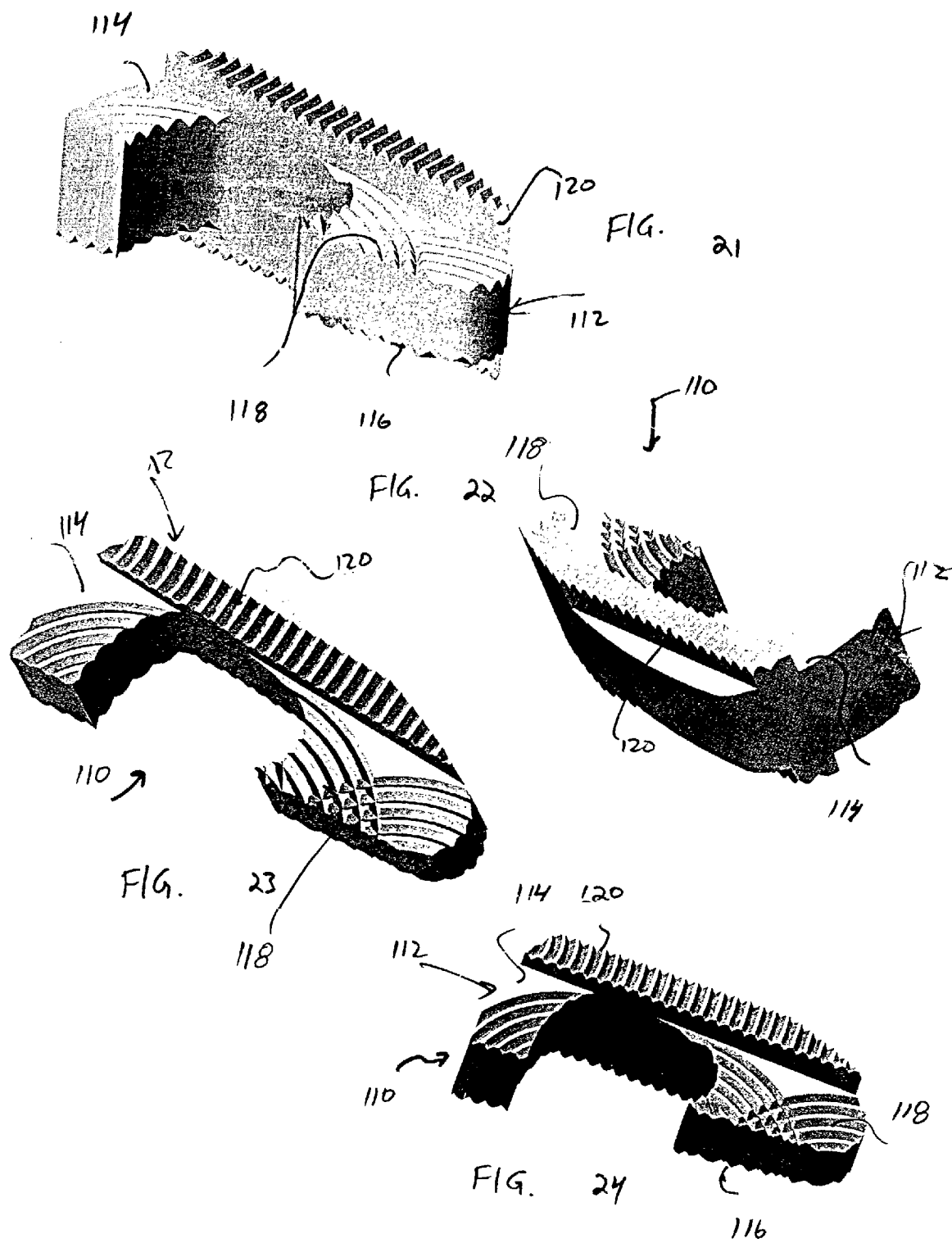

ALLOGRAFT SPINAL IMPLANT

This application claims priority to provisional patent applications which have been assigned U.S. Ser. No. 60/313,600 (filed Aug. 20, 2001) and U.S. Ser. No. 60/313,602 (filed Aug. 20, 2001).

FIELD OF THE INVENTION

The present invention generally pertains to orthopedic surgical procedures, and more particularly to an allograft spinal implant.

BACKGROUND OF THE INVENTION

In various orthopedic surgical procedures, it is necessary to secure portions of a spinal column in a relatively fixed relationship. This need is often a result of disease, damage or congenital deformation. For example, when one or more intervertebral disks of the spine degenerates due to trauma or disease, the spinal cord or emergent nerve can become compressed. This condition results in chronic and sometimes debilitating, neck, back, or peripheral pain.

One method of treatment for intervertebral disk degeneration involves surgical decompression of nerves, discectomy, and interbody fusion. Interbody fusion involves reestablishment of the normal gap between adjacent vertebral bodies. Heretofore, surgeons have employed various types of artificial implants and prostheses to stabilize the spinal column and promote fusion. The gap between adjacent vertebral bodies is commonly spanned with rigid spacer that is filled with bone graft material to facilitate bony fusion of the two vertebral bodies. A successful fusion stabilizes the spine, reduces pressure on the spinal cord and nerve roots, and reduces or eliminates back pain.

It is also known to insert harvested bone grafts or implants between adjacent vertebral bodies to maintain a normal gap. Such allografts comprise biological materials that are replaced over time with the patient's own bone through bone ingrowth. One common implant is referred to as a Cloward dowel. Cloward dowels are circular grafts made from autologous illiac crest bone. The dowels are bicortical, having porous cancellous bone between two cortical surfaces. A cylindrical cutting tool is typically used to prepare the cervical site to receive the dowel.

More recently, fibular and humeral cortical rings have been used as interbody spacers for spinal fusions such as anterior cervical fusions. Several tissue banks conventionally offer pre-shaped allograft cortical rings for this purpose.

While known devices for spinal fixation have proven to be effective in various applications to support the spinal column and promote fusion, they nevertheless can be the subject of certain improvements.

SUMMARY OF THE INVENTION

According to one aspect of the present invention, an allograft spinal implant is provided which resists migration and retropulsion from proper positioning within the spinal column.

A particular advantage of the present invention is to provide an allograft spinal implant which enhances bone fusion and resist migration or retropulsion in all directions in the plane of the vertebral body end plate/implant interfaces.

A related advantage of the present invention is to provide an allograft spinal implant having concentric circular ridges that resist migration or retropulsion.

A more particular advantage of the present invention is to provide an allograft spinal implant having concentric circular ridges with a common center positioned approximately at the centroid of a saggital section of a cortical shaft.

Another advantage of the present invention is to provide an allograft spinal implant having stabilizing fins that extend in superior and inferior directions.

Another advantage of the present invention is to provide an allograft spinal implant having one or more stabilizing fins that engage cooperating grooves in adjacent vertebrae extending in an anterior/posterior direction.

Additional advantages and features of the present invention will become apparent from the following description and appended claims, taken in conjunction with the accompanying drawings.

In one particular form, the present invention provides an allograft spinal implant including a generally planar superior end face, a generally planar inferior end face and a generally cylindrical sidewall. The generally cylindrical sidewall extends between the superior end face and the inferior end face. At least one of the superior end face and the inferior end face includes a plurality of concentric circular ridges.

In another particular form, the present invention provides an allograft spinal implant including a main body portion and at least one stabilizing fin. The main body portion includes a generally planar superior surface and a generally planar inferior surface. The at least one stabilizing fin extends from one of the superior surface and the inferior surface.

In yet another particular form, the present invention provides a method of stabilizing a spinal column. The method includes the step of providing a spinal implant having a main body portion with a generally planar superior surface and a generally planar inferior surface. The spinal implant further includes at least one stabilizing fin extending from one of the superior and inferior surfaces. The method additionally includes the step of disposing the spinal implant between a pair of adjacent vertebrae of the spinal column to establish a normal gap therebetween. Further, the method includes the step of engaging the at least one stabilizing fin in a corresponding groove formed in one of the pair of adjacent vertebrae.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
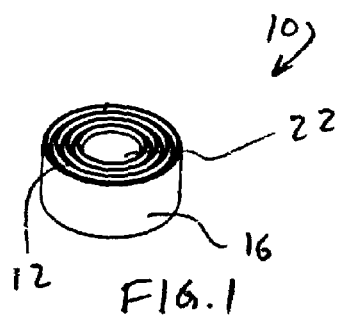
FIG. 1 is a perspective view illustrating an allograft spinal implant constructed in accordance with the teachings of a first preferred embodiment of the present invention.
Figure 2:
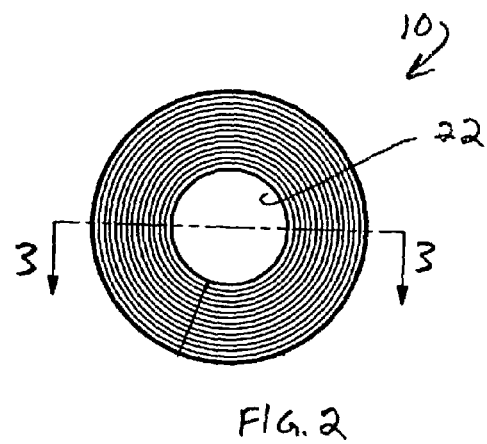
FIG. 2 is an inferior end view of the allograft spinal implant constructed according to the teachings of the first preferred embodiment of the present invention.
Figure 3:
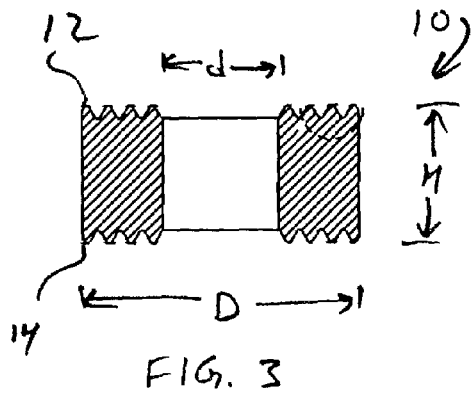
FIG. 3 is a cross-sectional view taken along the line 3—3 of FIG. 2.

The following description of the preferred embodiments of the present invention is merely exemplary in nature and is in no way intended to limit the invention or its application or uses.

With initial reference to FIGS. 1 through 4, an allograft spinal implant constructed in accordance with the teachings of a first preferred embodiment of the present invention is illustrated and generally identified at reference character 10. In one exemplary application, the spinal implant 10 of the first preferred embodiment of the present invention is particularly intended for cervical spine applications. However, those skilled in the art will readily appreciate that the teachings of the present invention are equally applicable for fusing other segments of the spinal column.

Figure 4:
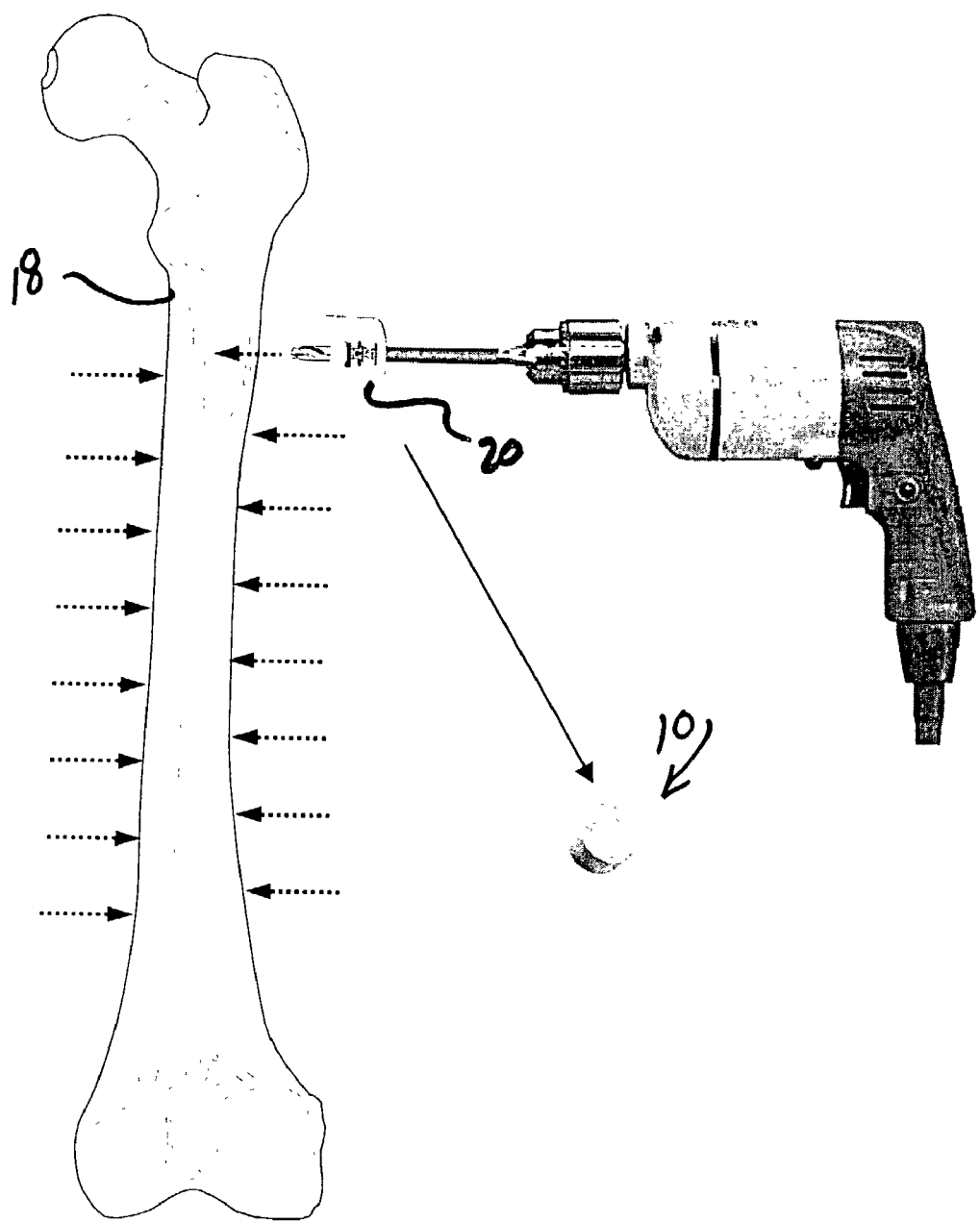
FIG. 4 is an environmental view illustrating a first general step for harvesting allograft spinal implants according to the teachings of the first preferred embodiment of the present invention.

The spinal implant 10 has a generally cylindrical shape having a generally planar and circular superior end 12, a generally planar and circular inferior end 14 and a generally cylindrical sidewall 16. In the preferred embodiment, the spinal implant 10 is harvested from a cortical shaft 18 with a power driven hole cutter 20 (see FIG. 4). The hole cutter generates rough cylinders of cortical tissue. The rough cylinders have concave and convex surfaces on the periosteal and endosteal surfaces, respectively, which are trimmed to so as to provide substantially planar and parallel ends 12 and 14 for abutting the end plates of adjacent vertebrae. In the view of FIG. 4, dashed arrows represent various points along the cortical shaft suitable for the harvesting of spinal implant 10.

The spinal implant 10 includes a centrally disposed and cylindrical shaped through hole 22. The through hole 22 can be packed with porous osteoconductive or osteoinductive graft material to promote bony through-growth and fusion. The ends 12 and 14 of the spinal implant 10 are formed to include a plurality of ridges particularly configured to prevent mitigation and retropulsion of the implant 10. As illustrated, the ridges 24 are prominent concentric-arc ridges 24 having a common center at the center of the through hole 22. The ridges 24 are applied to the implant 10 with a concentric-arc ridge cutter.

The implant 10 has an outer diameter D, a through hole diameter d and a height H. In certain preferred applications, the outer diameter or depth D ranges from approximately 8 mm to approximately 15 mm and the height H ranges from approximately 5 mm to 14 mm. In these particular applications, the diameter d of the through hole ranges from 0 mm, in which a through hole is not included, to approximately 6 mm.

Figure 5:
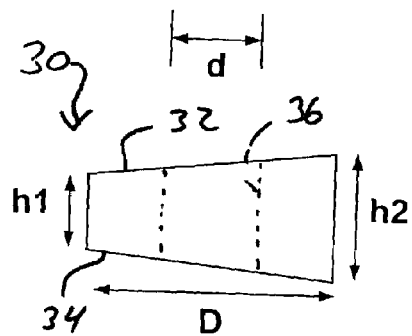
FIG. 5 is a simplified lateral side view illustrating an allograft spinal implant constructed according to the teachings of a second preferred embodiment of the present invention.

With reference to FIG. 5, a simplified lateral side view of an allograft spinal implant constructed according to the teachings of a second preferred embodiment of the present invention is generally identified at reference numeral 30. As with the first preferred embodiment, the implant is particularly intended for cervical spine applications. The implant 30 of the second preferred embodiment will be understood to be identical to the spinal implant 10 of the first preferred embodiment with the exception that superior and inferior end faces 32 and 34 of the implant 30 are not parallel to one another but relatively angled to accommodate natural spinal lordosis. In one exemplary application, the superior and inferior end faces 32 and 34 are angled from one another at approximately 5°. However, it is anticipated that the lordodic angle may fall within the range of 0° to approximately 10° or greater.

The implant 30 includes an anterior height h1, a posterior height h2, an outer diameter or depth D, and a through hole 36 having a diameter d. As with the spinal implant 10 of the first preferred embodiment, the through hole diameter d of the implant 30 preferably ranges from 0 mm to approximately 6 mm and the overall diameter or depth D preferably ranges from approximately 8 mm to approximately 15 mm. In these applications, the anterior height preferably ranges from approximately 8 mm to approximately 14 mm and the posterior height ranges from approximately 5 mm to approximately 11 mm.

Figure 6:
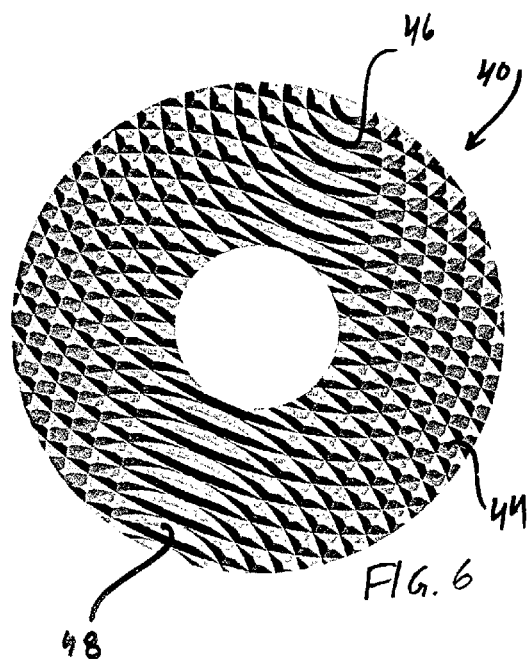
FIG. 6 is an inferior end view of an allograft spinal implant constructed according to the teachings of a third preferred embodiment of the present invention.
Figure 7:
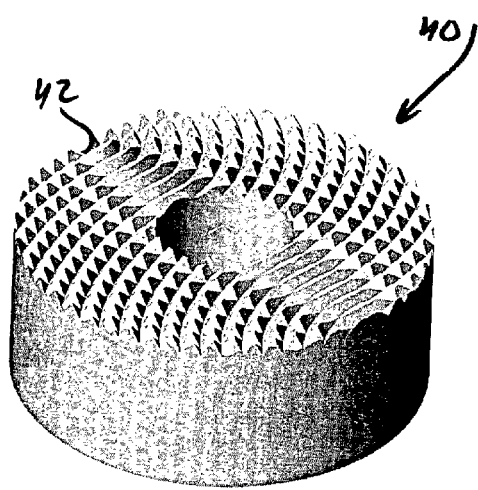
FIG. 7 is a perspective view of the allograft spinal implant constructed according to the teachings of the third preferred embodiment of the present invention.

Turning to FIGS. 6 and 7, an allograft spinal implant constructed according to the teachings of a third preferred embodiment of the present invention is generally identified at reference character 40. Implant 40 is similar to spinal implant 10 of the first preferred embodiment except that the superior and inferior end faces 42 and 44 incorporate an alternate ridge design. The illustrated ridge design includes first and second pluralities of ridges 46 and 48 having common centers on radially opposing sides of the implant 40.

Figure 8:
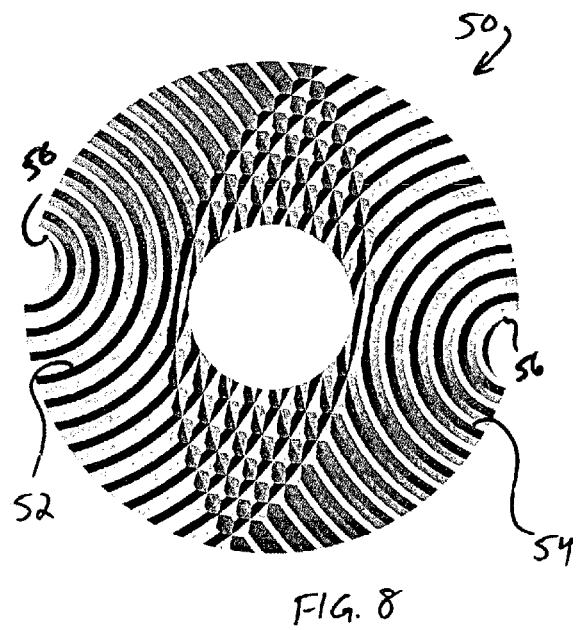
FIG. 8 is an inferior end view of an allograft spinal implant constructed according to the teachings of a fourth preferred embodiment of the present invention.
Figure 9:
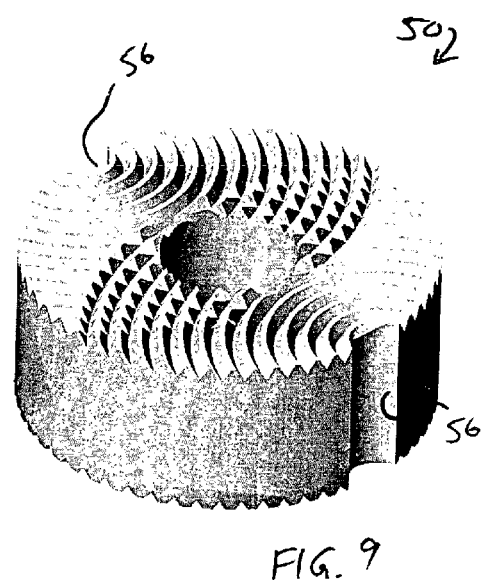
FIG. 9 is a perspective view of the allograft spinal implant constructed according to the teachings of the fourth preferred embodiment of the present invention.

With reference to FIGS. 8 and 9, an allograft spinal implant constructed in accordance with the teachings of a fourth preferred embodiment of the present invention is illustrated and generally identified at reference number 50. The implant 50 again includes first and second pluralities of ridges 52 and 54. The first and second pluralities of ridges 52 and 54 have common centers adjacent radially opposite sides of the implant 50. The implant 50 is further formed to include a pair of radially opposed notches 56 which can be grasped by an insertion tool (not shown) to facilitate implantation.

Figure 10:
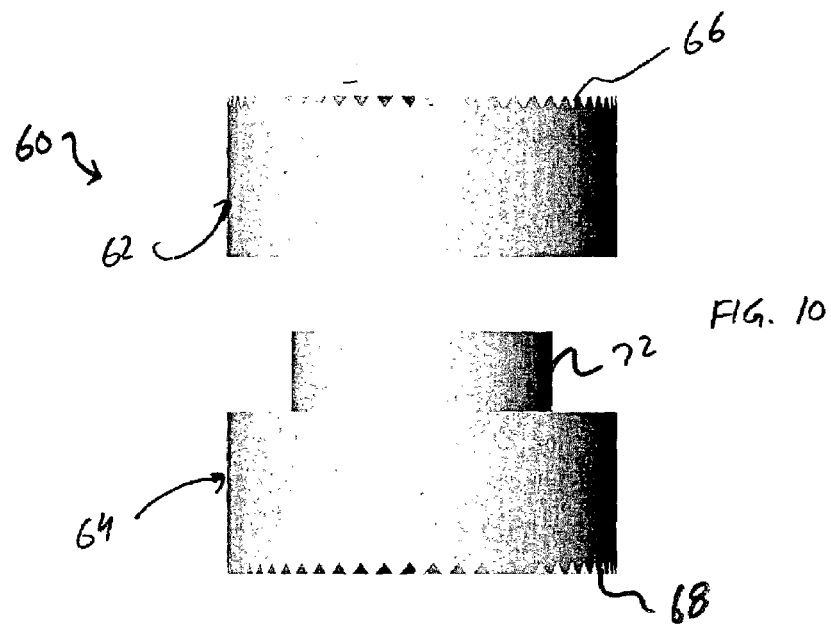
FIG. 10 is an exploded side view of an allograft spinal implant constructed according to the teachings of a fifth preferred embodiment of the present invention.
Figures 11, 12:
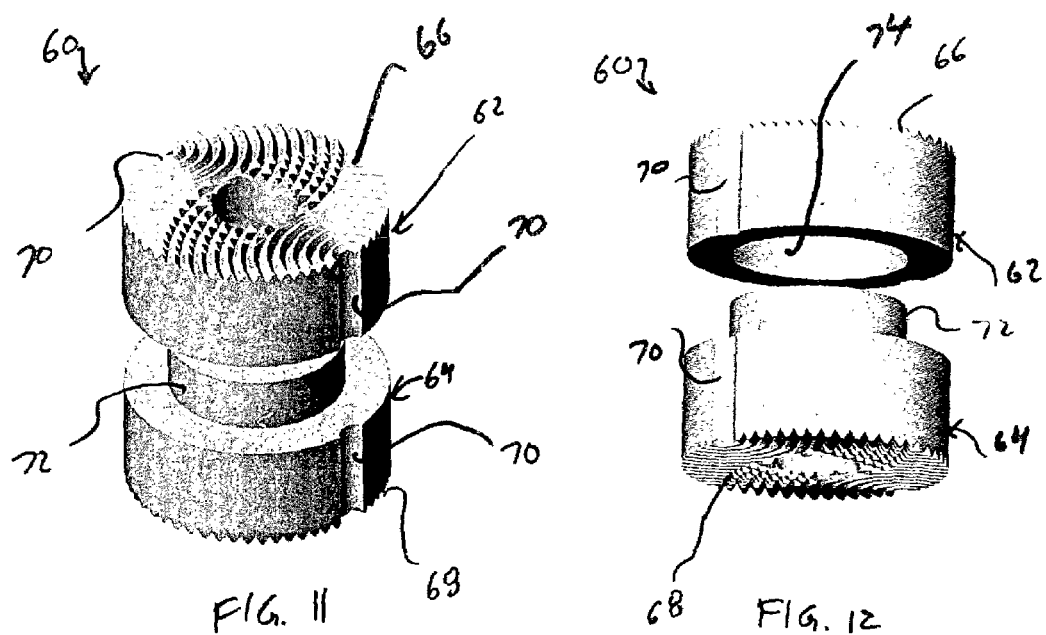
FIGS. 11 and 12 are exploded perspective views of the allograft spinal implant constructed according to the teachings of the fifth preferred embodiment of the present invention.
Figure 13:
FIG. 13 is a perspective view of an allograft spinal implant constructed according to the teachings of a sixth preferred embodiment of the present invention.
Figure 14:
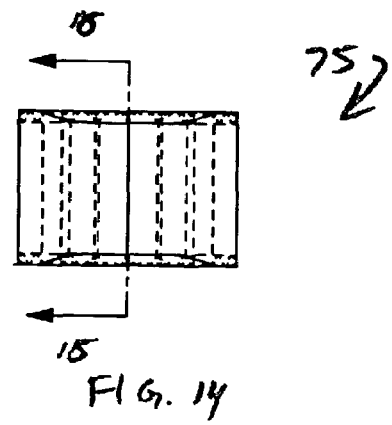
FIG. 14 is a side view of an allograft spinal implant constructed according to the teachings of the sixth preferred embodiment of the present invention.
Figure 15:
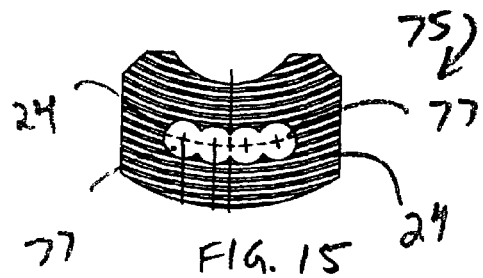
FIG. 15 is a superior end view of the allograft spinal implant constructed according to the teachings of the sixth preferred embodiment of the present invention.
Figure 16:
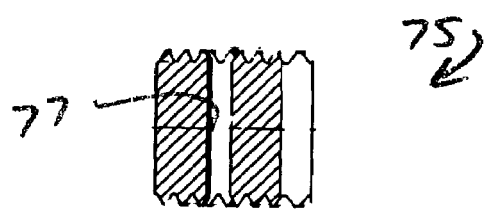
FIG. 16 is a cross-sectional view taken along the line 16—16 of FIG. 14.

With reference now to FIGS. 10–12, an allograft spinal implant constructed in accordance with the teachings of a fifth preferred embodiment of the present invention is illustrated and generally identified at reference character 60. Distinct from the embodiments previously disclosed, the implant 60 includes a two-part construction having an upper or superior component 62 and a lower or inferior component 64. The two-part design allows for a greater variety of finished implant sizes from a given donor skeleton. Further, the two-part design can be made from layers of cortical shafts with thinner cortical walls than allowable with a single cylindrical design thereby qualifying more weight-bearing donors for fabrication.

In the embodiment illustrated, the implant 60 includes substantially parallel end faces 66 and 68. The end faces 66 and 68 are shown to include a ridge pattern for resisting mitigation and retropulsion of the implant 60 substantially identical to that of the implant 50 of the fourth preferred embodiment. Also similar to the implant 50 of the fourth preferred embodiment, the implant 60 includes radially opposed notches 70. Alternatively, the implant 60 can be formed with angled end faces 66 and 68 to accommodate natural lordosis, alternate ridge patterns and without any notches 70.

The lower component 64 is shown to include an upwardly extending male portion 72 of reduced diameter. The male portion 72 is received in a press-fit within a cylindrical aperture 74 defined by the upper component 62.

With reference to FIGS. 13–16, a cervical allograft spinal implant constructed in accordance with the teachings of a sixth preferred embodiment of the present invention is illustrated and generally identified at reference character 75. The longitudinal axis of the donor bone is illustrated at arrow A. As with the first preferred embodiment, the implant 75 is illustrated to include a plurality of concentric-arc ridges 24 having a common center on both the inferior and superior surfaces. Distinct from the first embodiment, the implant 75 is only partially circular and is formed to include a plurality of through holes 77 extending from the inferior surface to the superior surface.

With reference to FIGS. 17–20, a cervical allograft spinal implant constructed in accordance with the teachings of a seventh preferred embodiment of the present invention is illustrated and generally identified at reference character 80. The implant 80 of the seventh preferred embodiment will be understood to be similar to the spinal implant 75 of the sixth preferred embodiment with the exception that superior and inferior end faces and of the implant 80 are not parallel to one another but relatively angled to accommodate natural spinal lordosis. In one exemplary application, the superior and inferior end faces 30 and 32 are angled from one another at approximately 9°. However, it is anticipated that the lordodic angle may fall within the range of 0° to approximately 9° or greater.

With reference to FIGS. 21–24, an allograft spinal implant constructed according to the teachings of an eighth preferred embodiment of the present invention is illustrated and generally identified at reference character 110. The implant 110 of the first preferred embodiment of the present invention is preferably fabricated from a diaphyseal shaft of a human tibia or femur. In one exemplary application, the spinal implant 110 is intended for posterior lumbar interbody spinal fusion applications. However, those skilled in the art will readily appreciate that certain teachings of the present invention are equally applicable for anterior lumbar spine fusion applications or fusing other segments of the spinal column.

The implant 110 includes a main body portion 112 including a generally planar superior surface 114 and a generally planar inferior surface 116. The main body portion is preferably at least partially ring-shaped. In the exemplary embodiment illustrated, the main body portion 112 is half ring-shaped. Further in the exemplary embodiment illustrated, the superior and inferior surfaces 114 and 116 are angled relative to one another at approximately 5°. Alternatively, it will be understood that the superior and inferior surfaces 114 and 116 may be parallel to one another or angled to a greater or lesser degree. Each of the superior and inferior surfaces 114 and 116 is shown to preferably include a ridge pattern 118 to prevent retropulsion and migration of the implant 110.

The implant 110 further includes at least one stabilizing fin 120 extending from at least one of the superior and inferior surfaces 114 and 116. In the embodiment illustrated, the implant 180 includes a first stabilizing fin 120 upwardly extending from the superior surface 114 and a second stabilizing fin 120 downwardly extending from the inferior surface 116. The stabilizing fins 120 are shown to be elongated in an anterior/posterior direction and preferably lie in a common plane.

Figure 25:
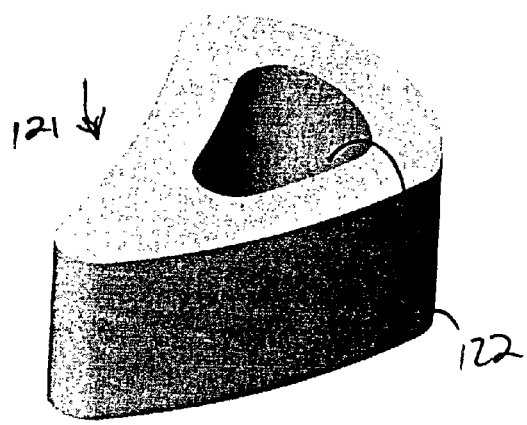
FIGS. 25–28 illustrate the manufacturing process for the allograft spinal implant according to the teachings of the eighth preferred embodiment of the present invention.

With reference to FIGS. 25–28, various stages of the implant 180 during a manufacturing process are illustrated. As shown in FIG. 25, a rough implant 121 is harvested from a transverse section of cortical bone. The rough implant 121 includes a through hole 122 that is naturally formed in the bone by the intramedullary canal.

Figure 26:
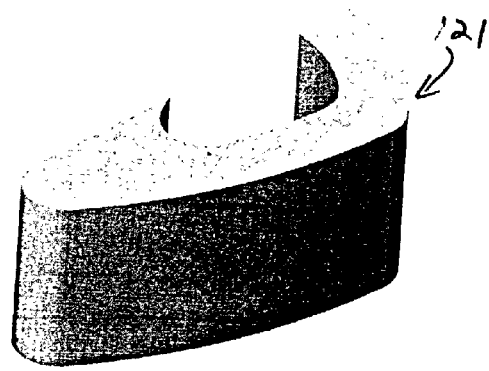

In the next intermediate step, which is shown in FIG. 26, the rough implant 121 is sawed so as to create a half ring shaped.

Figure 27:
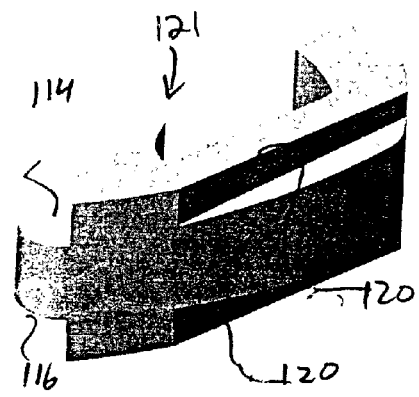

In FIG. 27, a third step is shown in which the rough implant 121 is milled so as to define the superior end face 114, the inferior end face 116 and the stabilizing fins 120. In the embodiment illustrated, the superior and inferior end faces 114 and 116 are disposed at a lordodic angle of approximately 6°. Alternatively, these surfaces may be formed so as to be parallel or angled to a greater or lesser degree. The superior and inferior surfaces of the stabilizing fins 120 are shown to be generally parallel to one another.

Figure 28:
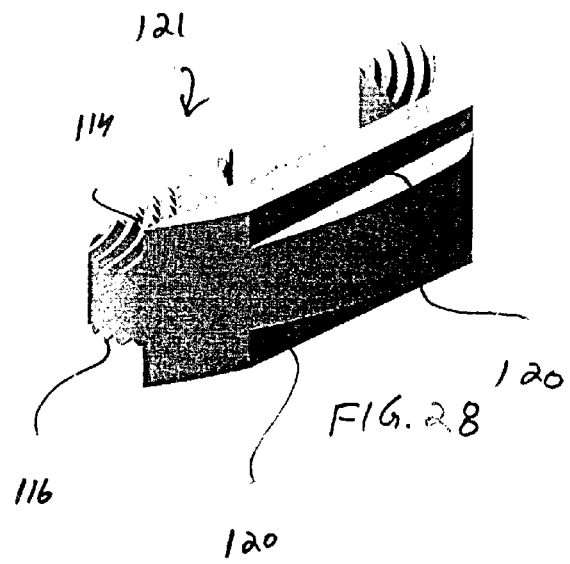

FIG. 28 illustrates the next step in which a ridge pattern is provided on the superior and inferior surfaces 114 and 16 with a concentric-arc ridge cutter (not shown).

In a final step, ridges are cut into the superior and inferior surfaces of the stabilizing fins 120 (as shown in FIGS. 21–24). In the embodiment illustrated, the ridges of the stabilizing fins 120 generally extend in a medial-lateral direction.

The implant 110 has as depth, a width, an anterior height, and a posterior height. In certain preferred applications, the depth ranges from approximately 14 mm to approximately 27 mm and the width W ranges from approximately 8 mm to 15 mm. In these particular applications, the anterior height, including the stabilizing fins 120, ranges from 7 mm to 28 mm and the posterior height ranges from 5 mm to 18 mm.

With reference to FIGS. 29–32, an exemplary use application for the implant 110 will be described. With particular reference to the simplified view of FIG. 31, a pair of implants 110 are shown surgically inserted between adjacent vertebrae V to reestablish a normal gap therebetween. The implants 110 are shown such that the stabilizing fins 120 are positioned on the lateral sides of the implant 110. The stabilizing fins 120 are disposed in corresponding grooves 126 provided in the end plate of the adjacent vertebrae.

With reference to FIGS. 33–36, an implant constructed according to the teachings of a ninth preferred embodiment of the present invention is generally identified at reference character 200. The implant 200 of the second preferred embodiment is identical to the implant 110 of the eighth preferred embodiment with the exception that the superior and inferior portions of the stabilizing fins are oriented at a lordodic angle of approximately 6°.

With to FIGS. 37–40, an allograft spinal implant constructed in accordance with the teachings of a tenth preferred embodiment of the present invention is illustrated and generally identified at reference character 210. Again, the implant 210 is particularly intended for posterior lumber interbody fusion. Arrow B indicates the long axis of the donor bone. In the embodiment illustrated, the sides of the implant 210 are formed to include grooves 212 to facilitate insertion. Inferior and superior surfaces of the implant 212 are formed to include a plurality of concentric-arc ridges 214.

With to FIGS. 41–44, an allograft spinal implant constructed in accordance with the teachings of a eleventh preferred embodiment of the present invention is illustrated and generally identified at reference character 230. As with the tenth preferred embodiment of the present invention, the implant 230 is particularly intended for posterior lumber interbody fusion. Distinct from the tenth preferred embodiment, the ridges 214 of the implant are only formed on a central strip.

With to FIGS. 45–48, an allograft spinal implant constructed in accordance with the teachings of a twelfth preferred embodiment of the present invention is illustrated and generally identified at reference character 250. The implant 250 is particularly intended for anterior lumbar interbody fusion applications. The long axis of the donor bone is indicated by arrow C. The implant 250 defines a generally central aperture 252. As with various prior embodiments of the present invention, the implant 250 is formed to include a plurality of concentric-arc ridges 254 on both the inferior and superior surfaces. In the embodiment illustrated, the superior and inferior end faces are angled from one another at approximately 6°. However, it is anticipated that the lordodic angle may fall within the range of 0° to approximately 6° or greater than 6°

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention. Particularly in this regard, the various dimensions identified herein with respect to the preferred embodiments will be understood to be merely exemplary applications. Those skilled in the art will appreciate that many factors (including but not limited to intended applications, particular patients, and the like) will necessarily require departure from the identified dimensions.

What is claimed is:

1. An allograft spinal implant comprising:
   a generally planar superior end face;
   a generally planar inferior end face; and
   a first generally curved sidewall extending between the superior end face and the inferior end face, the first sidewall terminating at first and second generally planar end walls extending between the superior end face and the interior end face, the first and second end walls both angularly crossing the first generally curved sidewall;

at least one of the superior end face and the inferior end face having a plurality of concentric circular arc continuous non-serrated ridges, at least some of the concentric circular arc continuous ridges of the plurality of concentric circular arc continuous ridges extending from the first end wall to the second end wall.

2. The allograft spinal implant spacer of claim 1, wherein the spacer is toroidal.

3. The allograft spinal implant spacer of claim 1, wherein the first sidewall comprises a circular arc.

4. The allograft spinal implant spacer of claim 1, wherein both of the superior end face and the inferior end face have a plurality of concentric circular arc continuous ridges.

5. The allograft spinal implant spacer of claim 3, wherein the first generally curved sidewall is an outer sidewall.

6. The allograft spinal implant spacer of claim 5, further comprising a second generally curved sidewall that is an inner sidewall.

7. The allograft spinal implant spacer of claim 6, wherein the radius of curvature of the second generally curved sidewall is distinct from the radius of curvature of the first generally curved sidewall.

8. The allograft spinal implant spacer of claim 6, wherein the radius of curvature of the second generally curved sidewall is smaller than the radius of curvature of the first generally curved sidewall.

9. The allograft spinal implant spacer of claim 6, further comprising at least one aperture extending from the generally planar superior end face to the generally planar inferior end face between the first and second generally curved sidewalls.

10. The allograft spinal implant spacer of claim 6, further comprising a plurality of apertures extending from the generally planar superior end face to the generally planar inferior end face between the first and second generally curved sidewalls.

11. The allograft spinal implant spacer of claim 3, wherein the generally planar superior end face is angled relative to the generally planar inferior end face.

12. The allograft spinal implant spacer of claim 11, wherein the second generally curved sidewall has a height greater than the first generally curved sidewall.

13. An allograft spinal implant comprising:
a generally planar superior end face;
a generally planar inferior end face; and
first and second generally curved sidewalls extending between the superior end face and the inferior end face; and terminating at first and second generally planar end walls extending between the superior end face and the inferior end face, the first and second end walls both angularly crossing the first generally curved sidewall;
wherein at least one of the superior and inferior end faces has a plurality of concentric circular arc continuous non-serrated ridges; and
wherein the first and second generally curved sidewalls and the ridges of the plurality of concentric circular arc continuous ridges each have a center of curvature along a common imaginary line.

14. The allograft spinal implant spacer of claim 13, wherein both of the superior end face and the inferior end face have a plurality of concentric circular arc continuous ridges.

15. The allograft spinal implant spacer of claim 13, wherein the radius of curvature of the second generally curved sidewall is distinct from the radius of curvature of the first generally curved sidewall.

16. The allograft spinal implant spacer of claim 13, wherein the radius of curvature of the second generally curved sidewall is smaller than the radius of curvature of the first generally curved sidewall.

17. The allograft spinal implant spacer of claim 13, further comprising at least one aperture extending from the generally planar superior end face to the generally planar inferior end face between the first and second generally curved sidewalls.

18. The allograft spinal implant spacer of claim 13, further comprising a plurality of apertures extending from the generally planar superior end face to the generally planar inferior end face between the first and second generally curved sidewalls.

19. The allograft spinal implant spacer of claim 13, wherein the generally planar superior end face is angled relative to the generally planar inferior end face.

20. An allograft spinal spacer comprising:
a first curved sidewall having an outer generally convex surface, an inner surface, and generally planar superior and inferior surfaces defining a first height therebetween;
a second curved sidewall having an outer generally concave surface, an inner surface facing the inner surface of the first curved sidewall, and generally planar superior and inferior surfaces defining a second height therebetween;
first and second generally planar end walls connecting the first curved sidewall to the second curved sidewall, the first and second generally planar end walls extending between the superior and inferior surfaces of the first and second curved sidewalls and oriented at an angle relative the outer and inner surfaces of the first and second curved sidewalls; and
a plurality of concentric arc continuous non-serrated ridges defined on the superior or inferior surface of at least one of the first and second sidewalls.

21. The allograft spinal spacer of claim 20, further comprising at least one aperture between the first and second sidewalls and extending along a superior-inferior direction.

22. The allograft spinal spacer of claim 20, wherein the first and second heights are unequal.

23. The allograft spinal spacer of claim 20, wherein the outer surface of the second curved sidewall comprises a circular arc.

* * * * *

UNITED STATES PATENT AND TRADEMARK OFFICE
CERTIFICATE OF CORRECTION

PATENT NO.           : 7,018,412 B2
APPLICATION NO. : 10/225090
DATED                   : March 28, 2006
INVENTOR(S)         : Ferreira et al.

It is certified that error appears in the above-identified patent and that said Letters Patent is hereby corrected as shown below:

The title page showing the illustrative figure should be deleted to be replaced with the attached title page.

The drawing sheets, (1-13) consisting of Figs. 1-48, should be deleted to be replaced with the drawing sheets, consisting of Figs. 1-48, as shown on the attached pages.

Signed and Sealed this

Twenty-fifth Day of March, 2008

JON W. DUDAS
*Director of the United States Patent and Trademark Office*

(12) United States Patent
Ferreira et al.

(10) Patent No.: US 7,018,412 B2
(45) Date of Patent: Mar. 28, 2006

(54) ALLOGRAFT SPINAL IMPLANT

(75) Inventors: Rui J. Ferreira, Newark, NJ (US); Jeffrey D. Schwardt, Morristown, NJ (US); Donald Kucharzyk, Crown Point, IN (US)

(73) Assignee: EBI, L.P., Parsippany, NJ (US)

( * ) Notice: Subject to any disclaimer, the term of this patent is extended or adjusted under 35 U.S.C. 154(b) by 0 days.

(21) Appl. No.: 10/225,090

(22) Filed: Aug. 20, 2002

(65) Prior Publication Data
US 2003/0069640 A1  Apr. 10, 2003

Related U.S. Application Data

(60) Provisional application No. 60/313,600, filed on Aug. 20, 2001, provisional application No. 60/313,602, filed on Aug. 20, 2001.

(51) Int. Cl.
*A61F 2/44* (2006.01)
(52) U.S. Cl. ............... 623/17.11; 623/17.15; 623/17.16; 606/61; 606/99
(58) Field of Classification Search ........... 623/17.11, 623/17.16, 17.15; 606/61, 99
See application file for complete search history.

(56) References Cited

U.S. PATENT DOCUMENTS

| | | | |
|---|---|---|---|
| 2,677,369 A | 4/1954 | Knowles | 128/92 |
| 4,714,469 A | 12/1987 | Kenna | 623/17 |
| 4,904,261 A | 2/1990 | Dove et al. | 623/17 |
| 4,950,296 A | 8/1990 | McIntyre | 623/16 |
| 5,112,354 A | 5/1992 | Sires | 623/16 |
| 5,489,308 A * | 2/1996 | Kuslich et al. | 623/17.11 |
| 5,728,159 A | 3/1998 | Stroever et al. | 623/16 |
| 5,814,084 A | 9/1998 | Grivas et al. | 623/16 |
| 5,865,845 A * | 2/1999 | Thalgott | 623/17.16 |
| 5,888,222 A | 3/1999 | Coates et al. | 623/17 |
| 5,989,289 A | 11/1999 | Coates et al. | 623/17 |
| 6,111,164 A | 8/2000 | Rainey et al. | 623/16 |
| 6,143,032 A | 11/2000 | Schafer et al. | 623/17.11 |
| 6,143,033 A | 11/2000 | Paul et al. | 623/17.11 |
| 6,206,923 B1 | 3/2001 | Boyd et al. | 623/17.11 |
| 6,277,149 B1 * | 8/2001 | Boyle et al. | 623/17.16 |
| 6,350,283 B1 | 2/2002 | Michelson | 623/17.11 |
| 6,511,509 B1 * | 1/2003 | Ford et al. | 623/23.5 |
| 2001/0039458 A1 | 11/2001 | Boyer, II et al. | 623/23.63 |
| 2001/0041941 A1 | 11/2001 | Boyer, II et al. | 623/23.52 |
| 2002/0091447 A1 | 7/2002 | Shimp et al. | 623/17.16 |
| 2002/0138143 A1 | 9/2002 | Grooms et al. | 623/17.11 |

FOREIGN PATENT DOCUMENTS

EP  0 599 419 A2  6/1994

\* cited by examiner

*Primary Examiner*—Thomas Barrett
*Assistant Examiner*—Christopher D Prone
(74) *Attorney, Agent, or Firm*—Harness, Dickey & Pierce, P.L.C.

(57) ABSTRACT

An allograft spinal implant includes a generally planar superior end face, a generally planar inferior end face and a generally cylindrical sidewall. The generally cylindrical sidewall extends between the superior end face and the inferior end face. At least one of the superior end face and the inferior end face includes a plurality of concentric circular ridges.

23 Claims, 13 Drawing Sheets

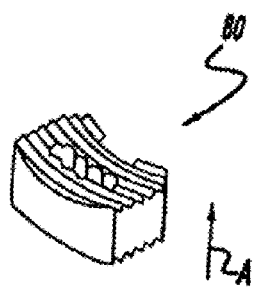

FIG-17

Figure 17:
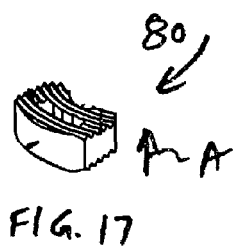
FIG. 17 is a perspective view of an allograft spinal implant constructed according to the teachings of a seventh preferred embodiment of the present invention.
Figure 18:
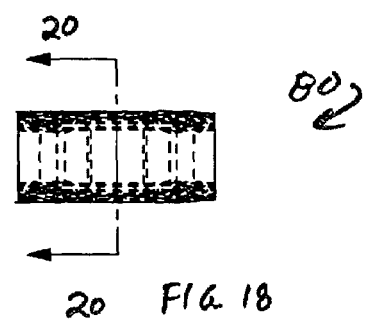
FIG. 18 is a side view of an allograft spinal implant constructed according to the teachings of the seventh preferred embodiment of the present invention.
Figure 19:
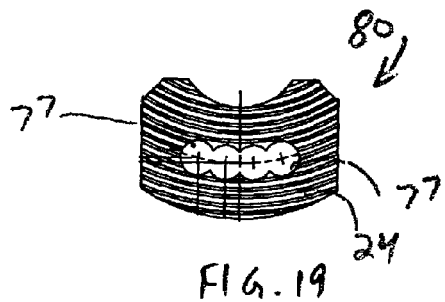
FIG. 19 is a superior view of the allograft spinal implant constructed according to the teachings of the seventh preferred embodiment of the present invention.
Figure 20:
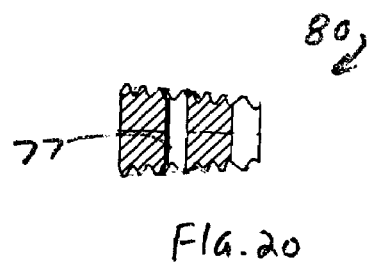
FIG. 20 is a cross-sectional view taken along the line 20—20 of FIG. 18.

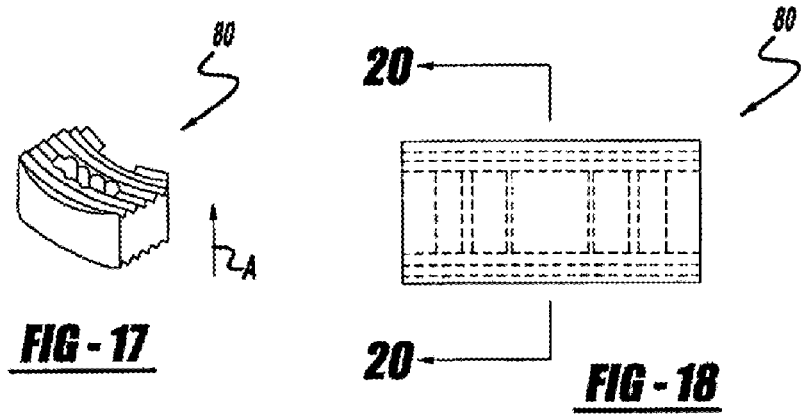
FIG - 17
FIG - 18
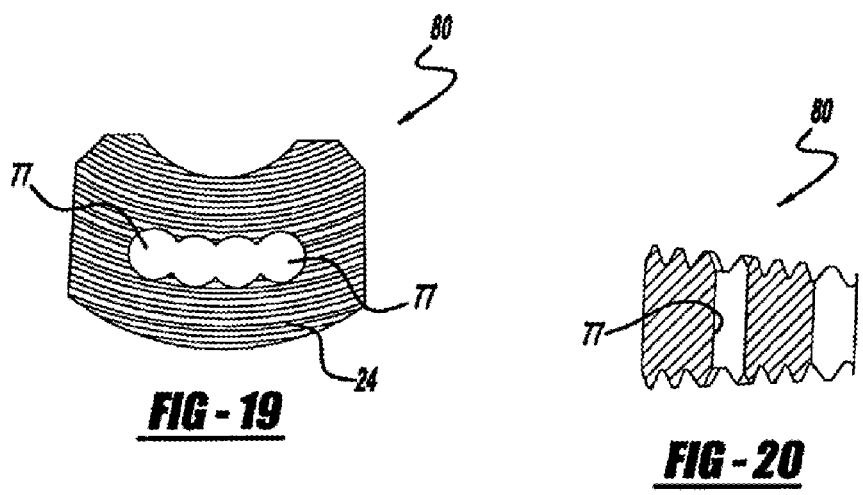
FIG - 19
FIG - 20

Figure 29:
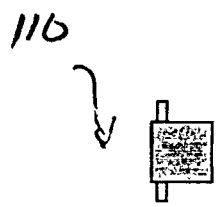
FIG. 29 is a simplified posterior side view of the allograft spinal implant according to the teachings of the eighth preferred embodiment of the present invention.
Figure 30:
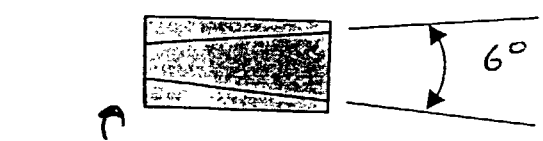
FIG. 30 is a simplified lateral side view of the allograft spinal implant according to the teachings of the eighth preferred embodiment of the present invention.
Figure 31:
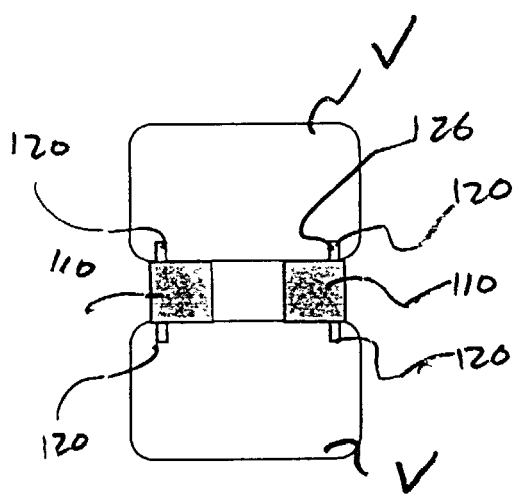
FIG. 31 is a simplified posterior view illustrating a pair of allograft spinal implants according to the teachings of the eighth preferred embodiment shown operatively positioned between a pair of adjacent vertebrae.
Figure 32:
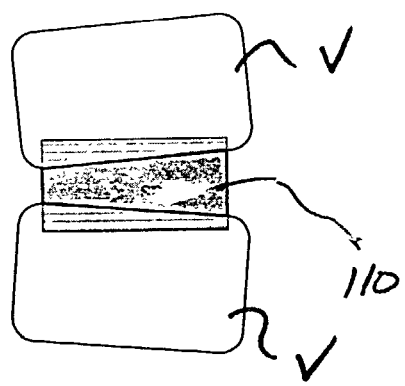
FIG. 32 is a simplified lateral view illustrating the allograft spinal implant according to the teachings of the eighth preferred embodiment shown operatively positioned between the pair of vertebrae.
Figure 33:
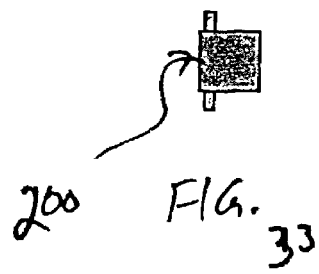
FIG. 33 is a simplified posterior side view of the allograft spinal implant according to the teachings of a ninth preferred embodiment of the present invention.
Figure 34:
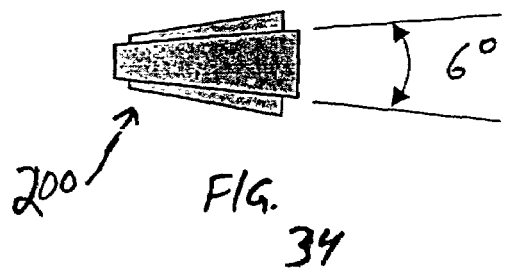
FIG. 34 is a simplified lateral side view of the allograft spinal implant according to the teachings of the ninth preferred embodiment of the present invention.
Figure 35:
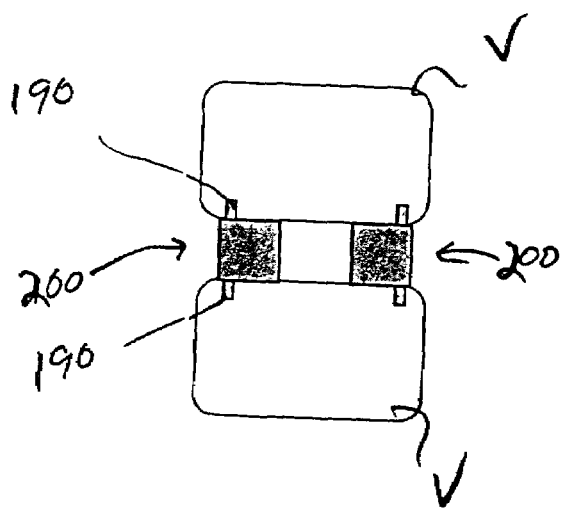
FIG. 35 is a simplified posterior view illustrating a pair of allograft spinal implants according to the teachings of the ninth preferred embodiment shown operatively positioned between a pair of adjacent vertebrae.
Figure 36:
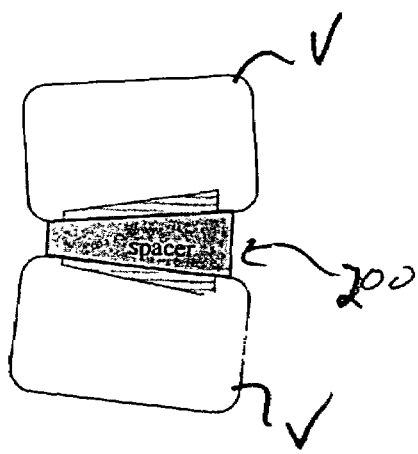
FIG. 36 is a simplified lateral view illustrating the allograft spinal implant according to the teachings of the ninth preferred embodiment shown operatively positioned between the pair of vertebrae.
Figure 37:
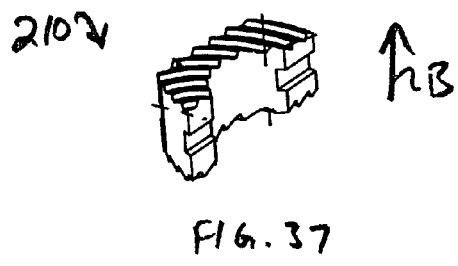
FIG. 37 is a perspective view of the allograft spinal implant constructed according to the teachings of a tenth preferred embodiment of the present invention.
Figure 38:
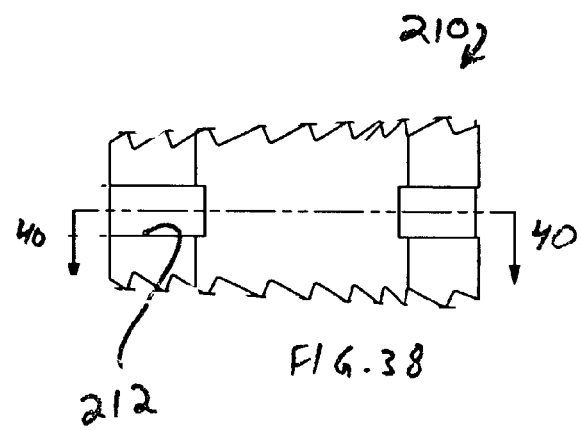
FIG. 38 is a side view of an allograft spinal implant constructed according to the teachings of the tenth preferred embodiment of the present invention.
Figure 39:
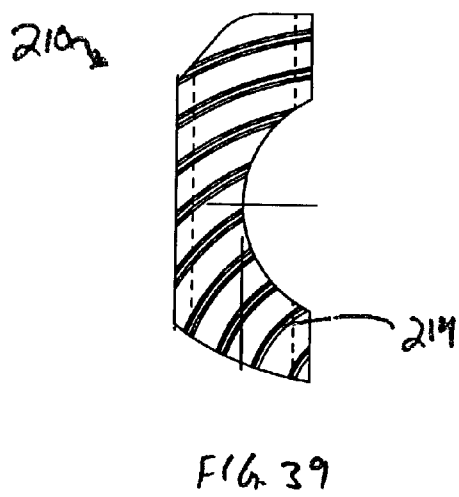
FIG. 39 is a superior end view of the allograft spinal implant constructed according to the teachings of the tenth preferred embodiment of the present invention.
Figure 40:
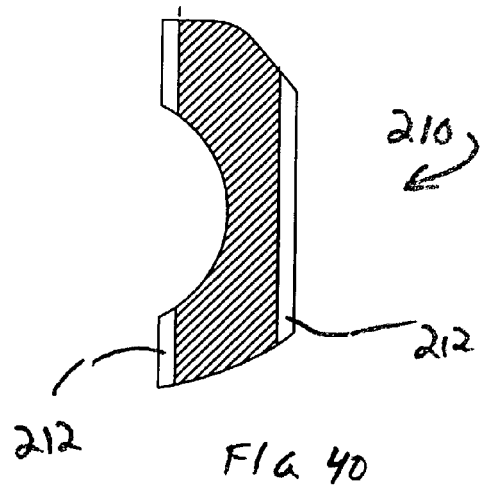
FIG. 40 is a cross-sectional view taken along the line 40—40 of FIG. 38.
Figure 41:
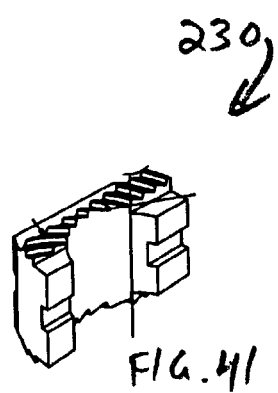
FIG. 41 is a perspective view of the allograft spinal implant constructed according to the teachings of an eleventh preferred embodiment of the present invention.
Figure 42:
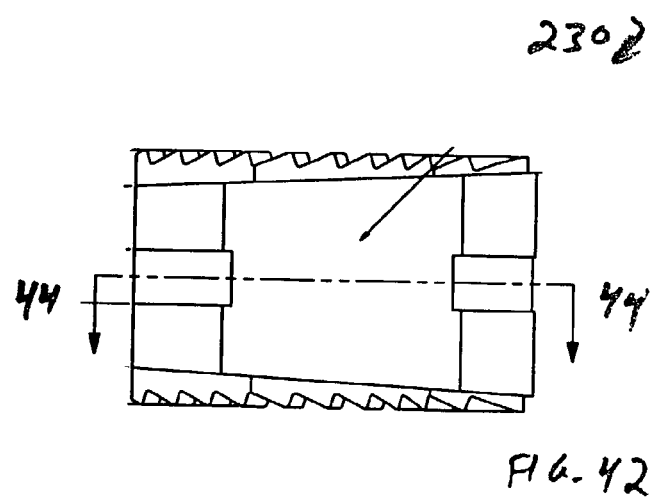
FIG. 42 is a side view of an allograft spinal implant constructed according to the teachings of the eleventh preferred embodiment of the present invention.
Figure 43:
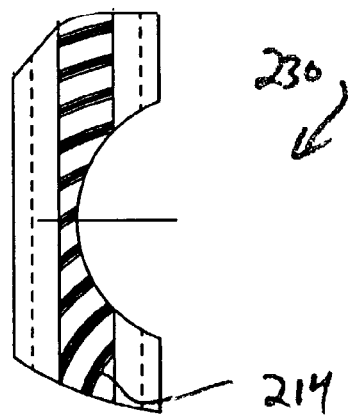
FIG. 43 is a superior end view of the allograft spinal implant constructed according to the teachings of the eleventh preferred embodiment of the present invention.
Figure 44:
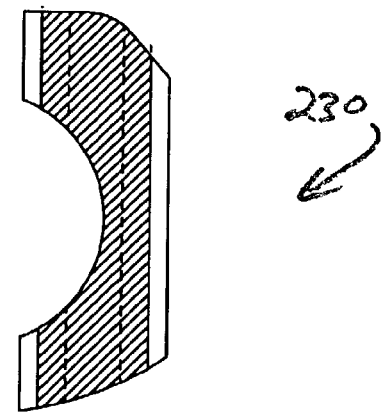
FIG. 44 is a cross-sectional view taken along the line 44—44 of FIG. 42.
Figure 45:
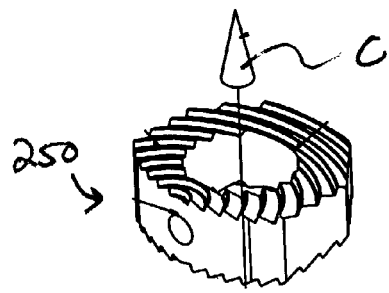
FIG. 45 is a perspective view of the allograft spinal implant constructed according to the teachings of a twelfth preferred embodiment of the present invention.
Figure 46:
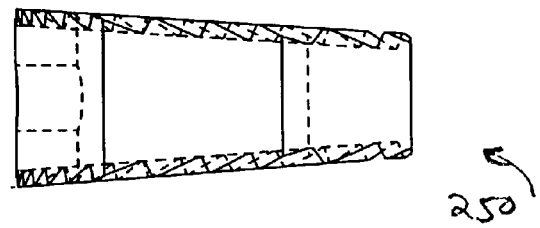
FIG. 46 is a side view of an allograft spinal implant constructed according to the teachings of the twelfth preferred embodiment of the present invention.
Figure 47:
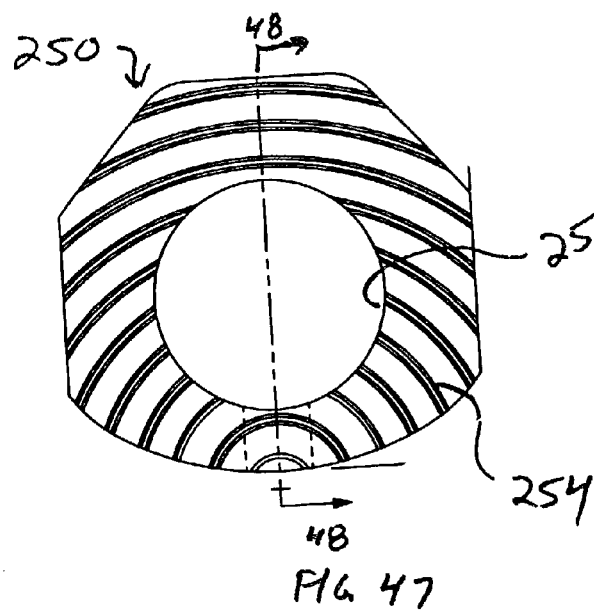
FIG. 47 is a superior end view of the allograft spinal implant constructed according to the teachings of the twelfth preferred embodiment of the present invention.
Figure 48:
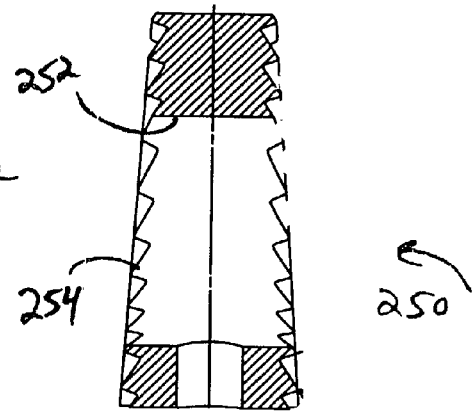
FIG. 48 is a cross-sectional view taken along the line 48—48 of FIG. 47.
Figure 1:
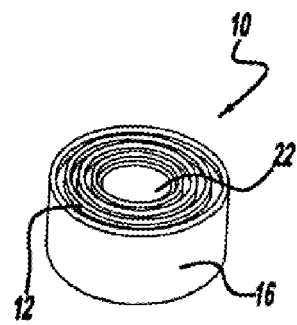
Figure 2:
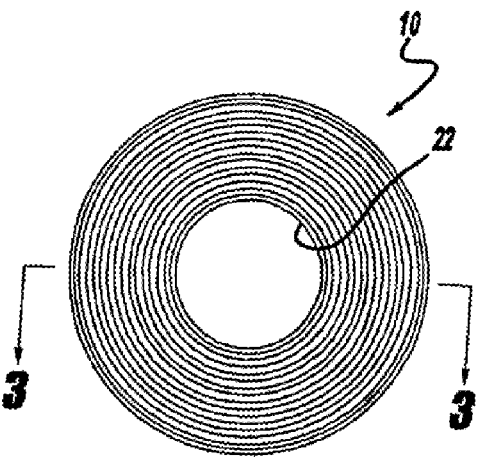
Figure 3:
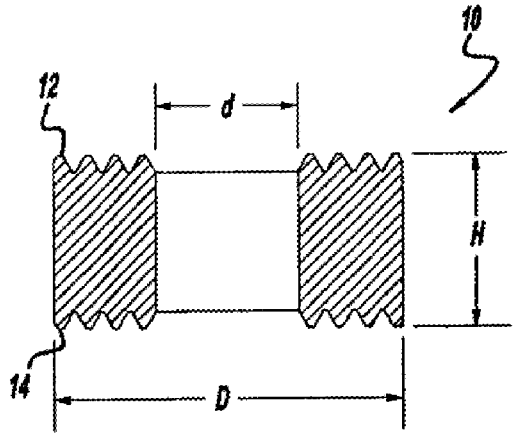
Figure 5:
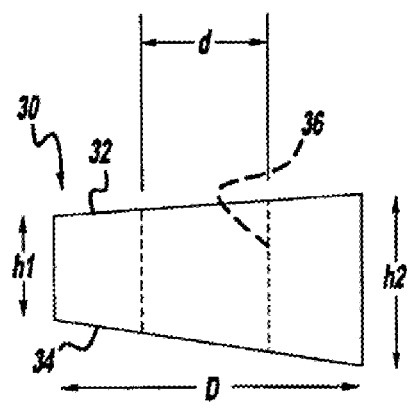
Figure 4:
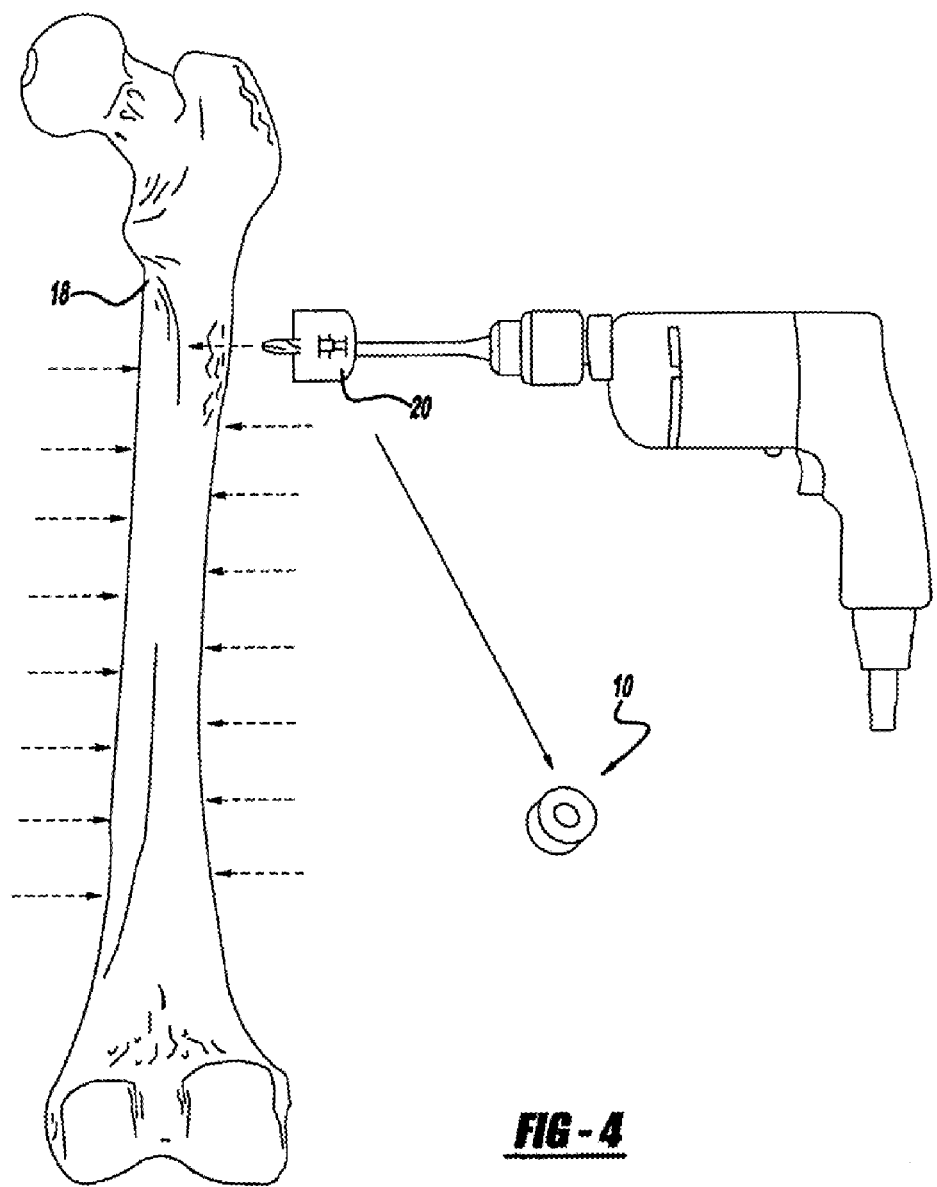
Figure 6:
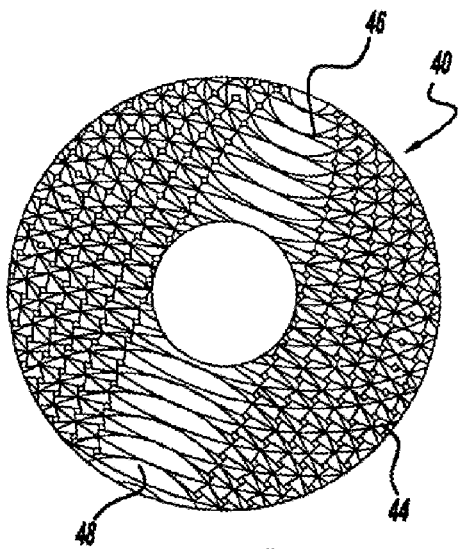
Figure 7:
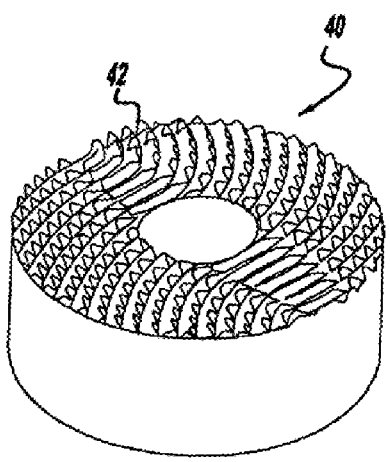
Figure 8:
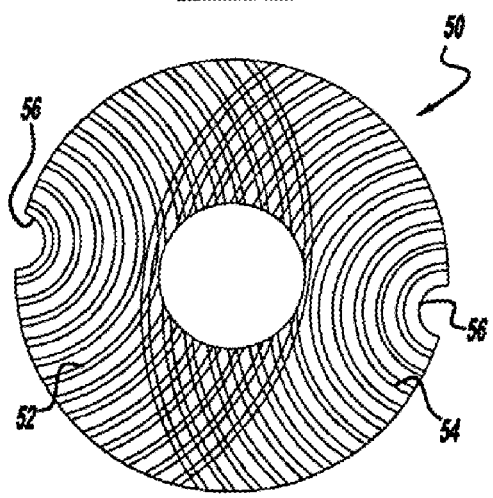
Figure 9:
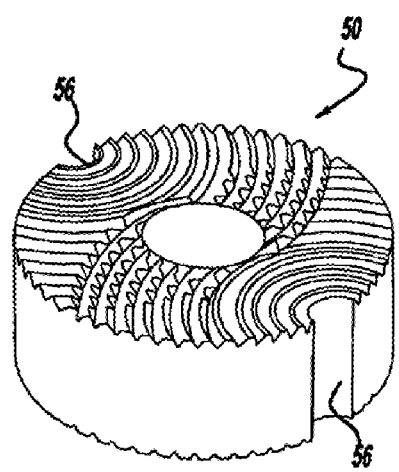
Figure 10:
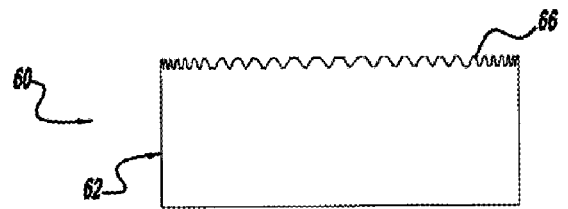
Figure 10:
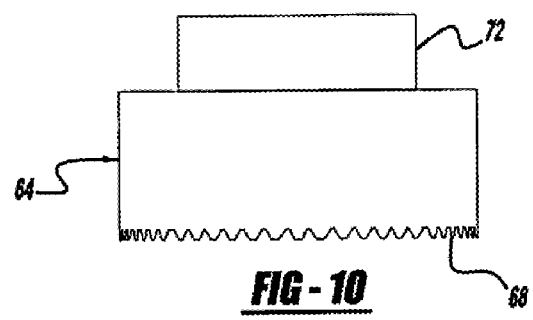
Figure 11:
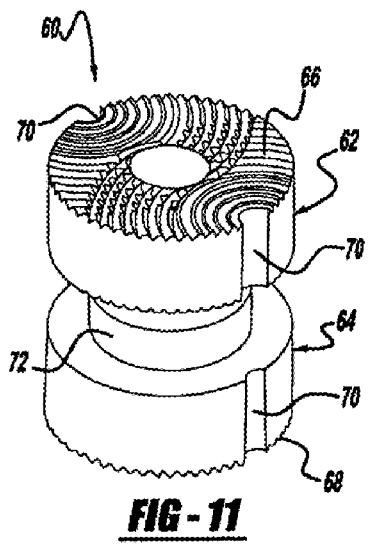
Figure 12:
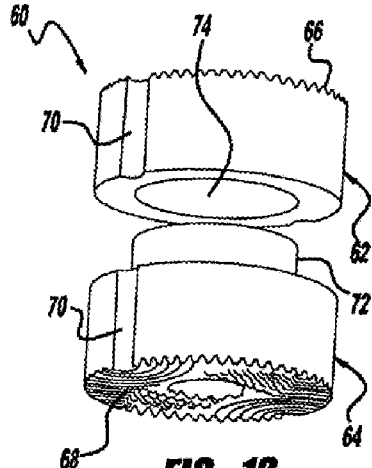
Figure 13:
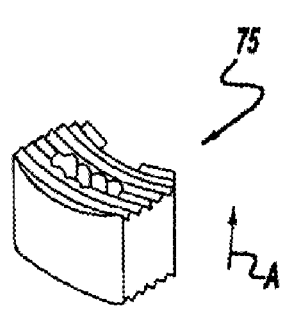
Figure 14:
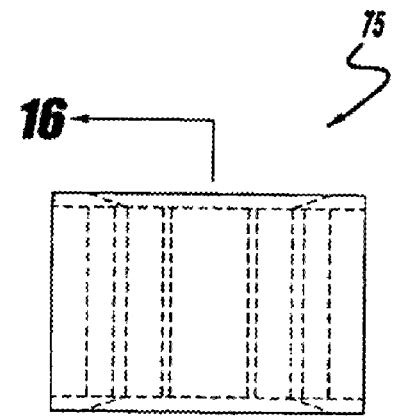
Figure 15:
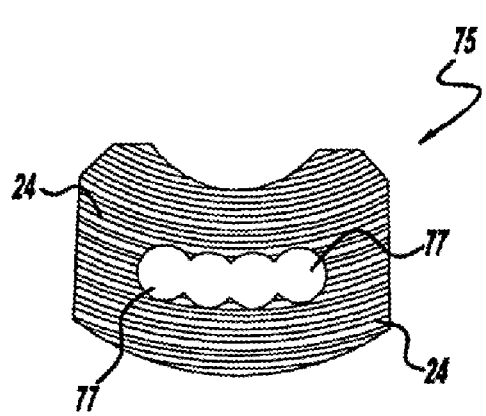
Figure 16:
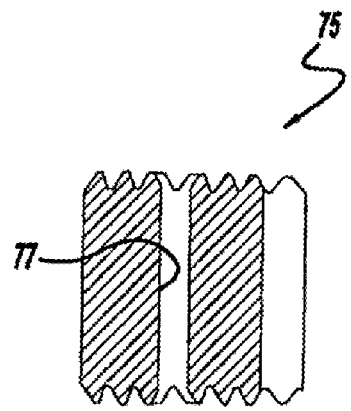
Figure 21:
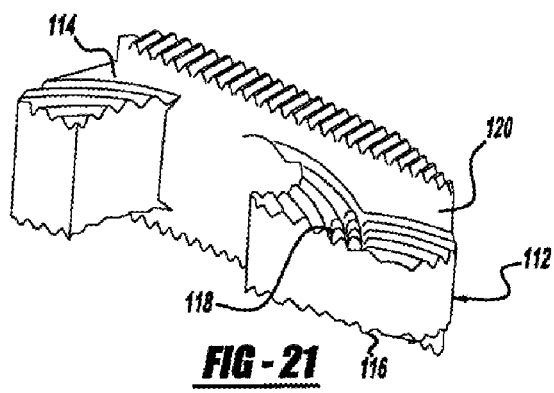
FIGS. 21–24 are various perspective views of the allograft spinal implant constructed according to the teachings of a eighth preferred embodiment of the present invention.
Figures 22, 23:
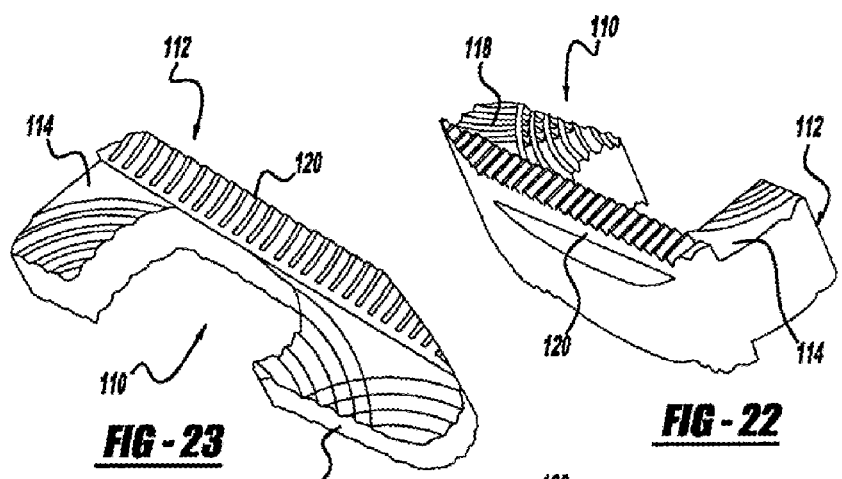
Figure 24:
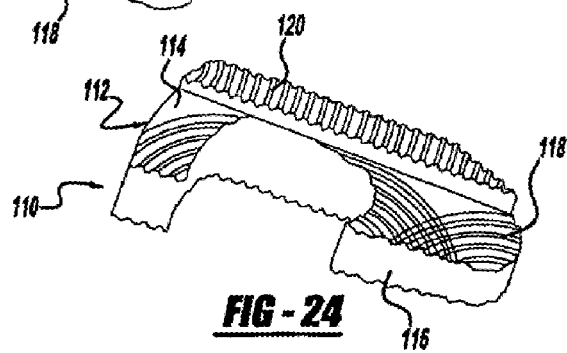
Figure 25:
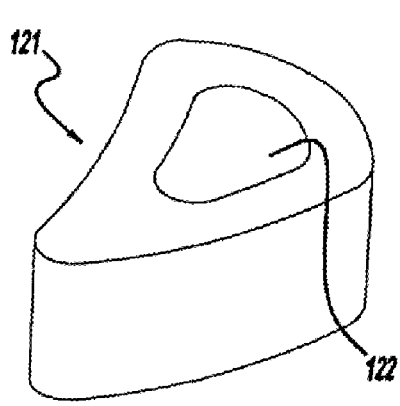
Figure 26:
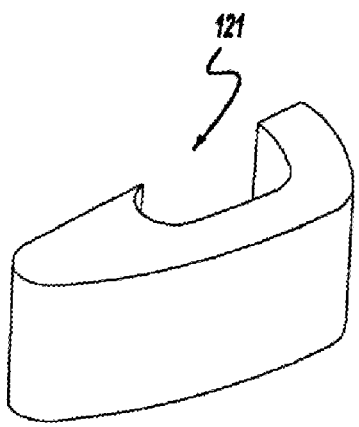
Figure 27:
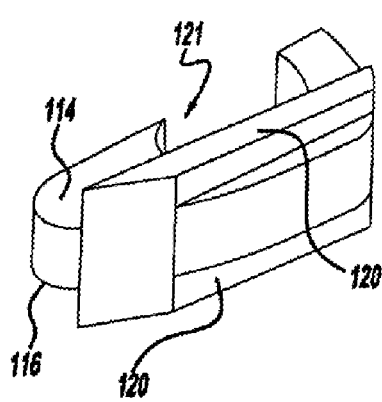
Figure 28:
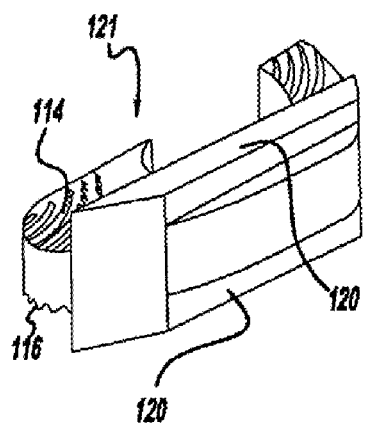
Figure 33:
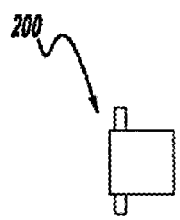
Figure 34:
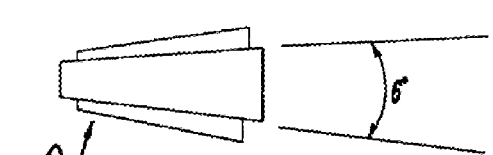
Figure 35:
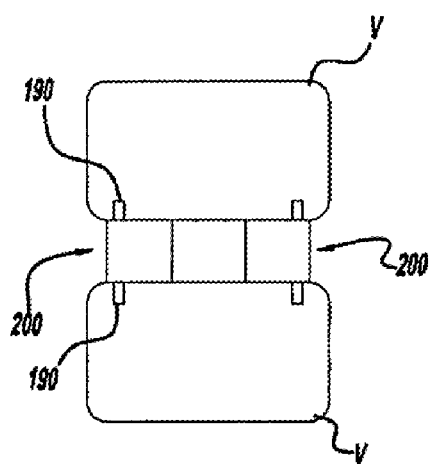
Figure 36:
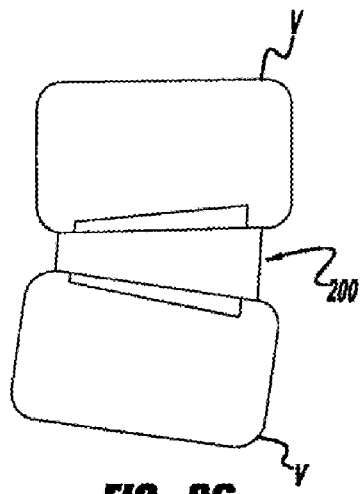
Figure 37:
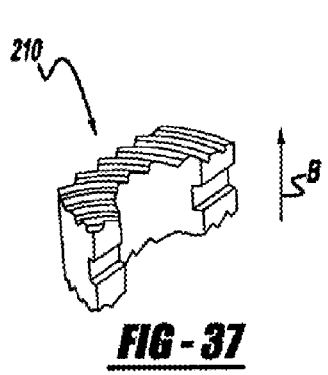
Figure 38:
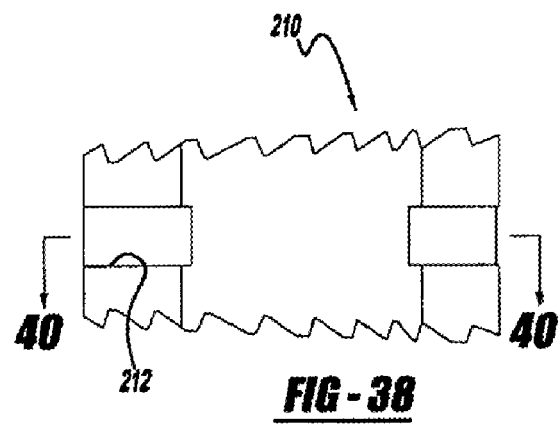
Figure 39:
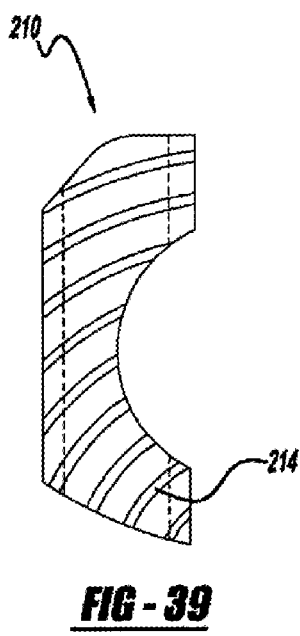
Figure 40:
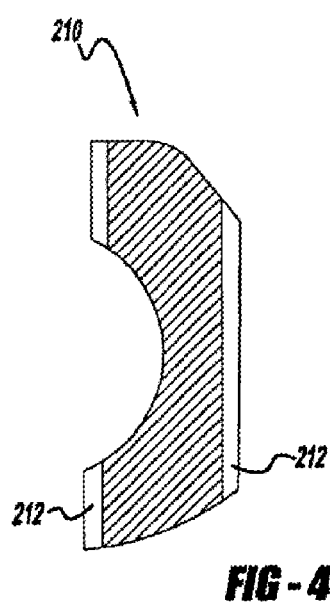
Figure 41:
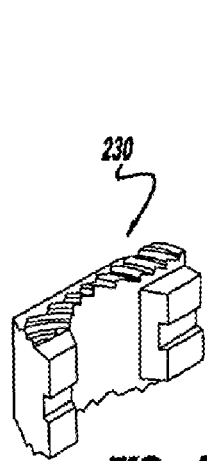
Figure 42:
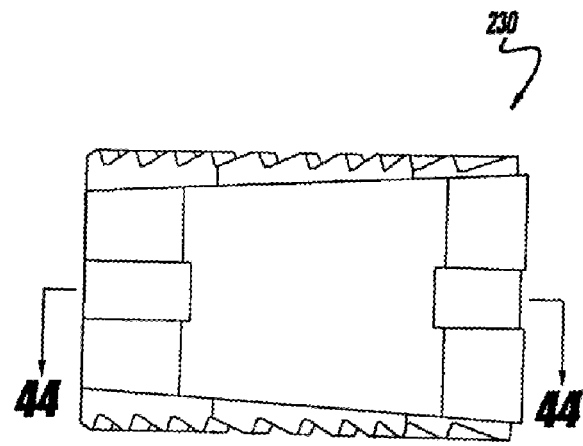
Figure 43:
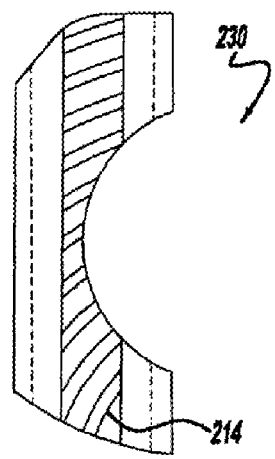
Figure 44:
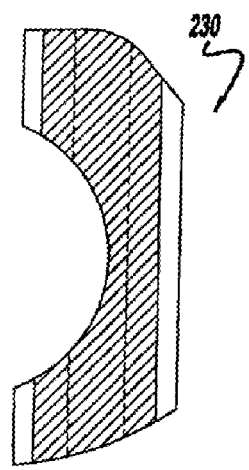
Figure 45:
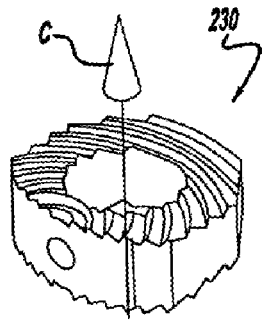
Figure 46:
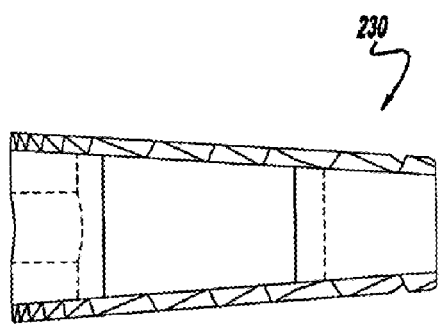
Figure 47:
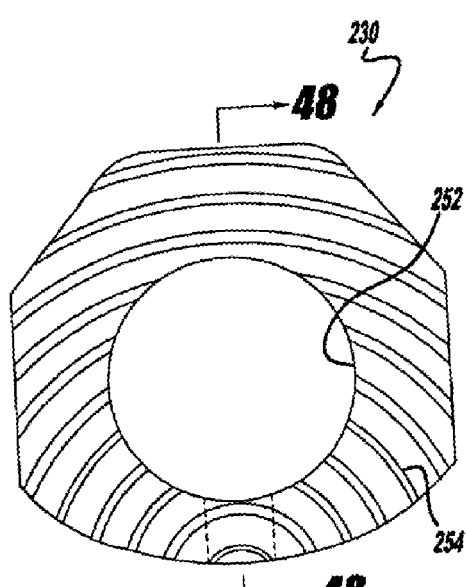
Figure 48:
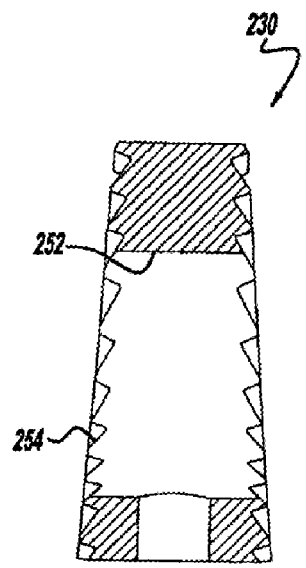

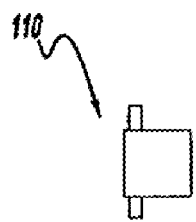
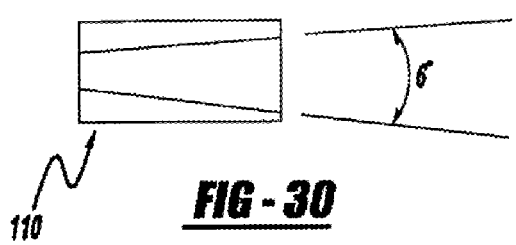
FIG - 29    FIG - 30
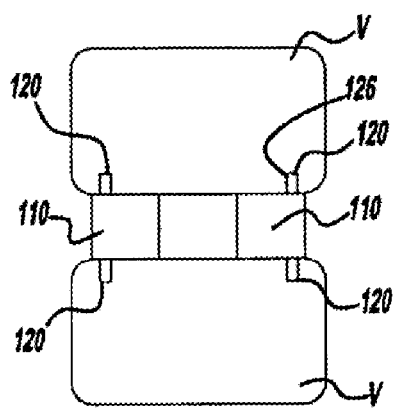
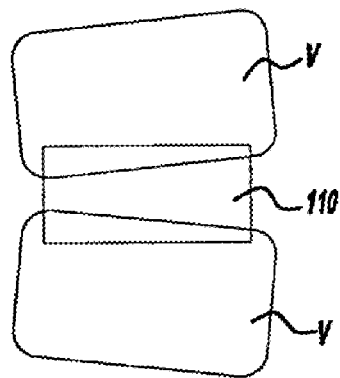
FIG - 31    FIG - 32